US012644590B2

(12) United States Patent
Bukkems et al.

(10) Patent No.: US 12,644,590 B2
(45) Date of Patent: Jun. 2, 2026

(54) LIGHT EMITTING DEVICE WITH HEAT SPACER

(71) Applicant: SIGNIFY HOLDING B.V., Eindhoven (NL)

(72) Inventors: Peter Bukkems, Deurne (NL); Martinus Arnoldus Cornelis Heijmans, Veldhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/294,222

(22) PCT Filed: Aug. 2, 2022

(86) PCT No.: PCT/EP2022/071616
§ 371 (c)(1),
(2) Date: Feb. 1, 2024

(87) PCT Pub. No.: WO2023/012134
PCT Pub. Date: Feb. 9, 2023

(65) Prior Publication Data
US 2024/0337375 A1 Oct. 10, 2024

(30) Foreign Application Priority Data

Aug. 3, 2021 (EP) ..................................... 21189292

(51) Int. Cl.
*F21V 29/71* (2015.01)
*F21V 29/503* (2015.01)
(Continued)

(52) U.S. Cl.
CPC .......... *F21V 29/713* (2015.01); *F21V 29/503* (2015.01); *F21V 29/51* (2015.01);
(Continued)

(58) Field of Classification Search
CPC ...... F21V 29/713; F21V 29/74; F21V 29/503; F21Y 2115/00; F21Y 2115/10; F21S 8/026
See application file for complete search history.

(56) References Cited

U.S. PATENT DOCUMENTS 6,545,879 B1 * 4/2003 Goodwin ............. H05K 7/1053
361/709
2001/0030866 A1 * 10/2001 Hochstein ........... H10F 77/1215
362/547
(Continued)

FOREIGN PATENT DOCUMENTS

CN 106338035 A * 1/2017
CN 206514179 U 9/2017
(Continued)

OTHER PUBLICATIONS

Search English translation of CN-106338035-A (Year: 2017).*
Search English translation of KR-101095868-B1 (Year: 2011).*
Search English translation of DE 102006001711 B4 (Year: 2008).*

*Primary Examiner* — Omar Rojas Cadima

(57) ABSTRACT

A light emitting device comprising a light source, a housing, a casing and a heat sink element, the casing comprising a connection surface, the heat sink element comprising a first part configured to be connected to the light source, and a second part configured to be connected to the first part, wherein the first part comprises a first connection structure and the second part comprises a second connection structure, and wherein the first connection structure and the second connection structure are configured to, in a mounted condition, be in mutual contact with one another for transferring heat from the first part to the second part.

12 Claims, 12 Drawing Sheets

(51) Int. Cl.

| | | |
|---|---|---|
| *F21V 29/51* | (2015.01) | |
| *F21V 29/74* | (2015.01) | |
| *A61L 2/08* | (2006.01) | |
| *A61L 2/26* | (2006.01) | |
| *F21Y 113/00* | (2016.01) | |
| *F21Y 115/00* | (2016.01) | |

(52) U.S. Cl.
CPC ................. *F21V 29/74* (2015.01); *A61L 2/08* (2013.01); *A61L 2/26* (2013.01); *A61L 2202/11* (2013.01); *F21Y 2113/00* (2013.01); *F21Y 2115/00* (2016.08)

(56) References Cited

U.S. PATENT DOCUMENTS

| | | | |
|---|---|---|---|
| 2011/0316417 A1 | 12/2011 | Chen | |
| 2012/0002429 A1 | 1/2012 | Watanabe et al. | |
| 2012/0106140 A1* | 5/2012 | Sun ......................... | F21K 9/232 |
| | | | 29/825 |
| 2012/0182737 A1* | 7/2012 | Kuenzler .............. | F21V 19/003 |
| | | | 362/249.02 |
| 2013/0003378 A1 | 1/2013 | Dube et al. | |
| 2013/0258677 A1 | 10/2013 | Fryzek et al. | |
| 2015/0219331 A1 | 8/2015 | Clark | |
| 2015/0260388 A1 | 9/2015 | Geels et al. | |
| 2019/0017667 A1* | 1/2019 | Mitchell ............... | F21V 29/713 |

FOREIGN PATENT DOCUMENTS

| | | | | |
|---|---|---|---|---|
| CN | 208832271 U | 5/2019 | | |
| DE | 102006001711 B4 * | 10/2008 | ........... | F21S 41/151 |
| KR | 20100034588 A | 4/2010 | | |
| KR | 101095868 B1 * | 12/2011 | | |

* cited by examiner

5

52

51

6

51

52

XPlane Plot3 Temperature 94.680°C

XPlane Plot Temperature 95.358°C

XPlane Plot2 Temperature 94.943°C

XPlane Plot4 Temperature 96.076°C

XPlane Plot1 Temperature 95.138°C

Temperature (°C)

100.00
98.571
97.143
95.714
94.286
92.857
91.429
90.000

XPlane Plot3
Temperature 94.405°C

XPlane Plot
Temperature 95.717°C

XPlane Plot2
Temperature 94.715°C

XPlane Plot4
Temperature 97.440°C

XPlane Plot1
Temperature 95.320°C

Temperature (°C)

100,00
98,571
97,143
95,714
94,286
92,857
91,429
90,000

LIGHT EMITTING DEVICE WITH HEAT SPACER

CROSS-REFERENCE TO PRIOR APPLICATIONS

This application is the U.S. National Phase application under 35 U.S.C. § 371 of International Application No. PCT/EP2022/071616, filed on Aug. 2, 2022, which claims the benefit of European Patent application Ser. No. 21/189, 292.2, filed on Aug. 3, 2021. These applications are hereby incorporated by reference herein.

TECHNICAL FIELD

The present invention relates to a lighting device comprising a light source and a heat transfer unit.

BACKGROUND

It is known that lighting devices also produce heat as unwanted effect, and that therefore they intrinsically constitute a thermal challenge. Heat sinks are arranged to keep the temperature of the lighting device as low as possible in order to increase lifetime, which is strongly related to the operation temperature. The market trend of wanting to have more and more light out of the same form factor implies that the thermal challenge becomes bigger and alternative solutions are needed.

Efforts have been made to at least reduce the temperature of lighting devices with different heat sinks solutions. One example of such a lighting device is a LED lighting device as disclosed in US 2012/002429 A1, where the heat generated by the light source is conducted from the cap portion of the light device to the fixture body. Another example is luminaires with casing, represented in FIG. 1, where a compact heat sink surrounds the light source. Those solutions, however, are not efficient enough in the case of higher or increased light output from a defined or constant form factor.

In view of the above, it is desired to obtain a light emitting device with a thermal management system with improved heat dissipation compared to the solutions suggested by the prior art.

SUMMARY

It is an object of the present invention to provide a lighting device that alleviates the above-mentioned drawbacks of the prior art and is more effective.

In accordance with the present invention, the object is achieved with a light emitting device comprising a light source, a housing, a casing and a heat sink element, the casing comprising a connection surface, the heat sink element comprising a first part configured to be connected to the light source, and a second part configured to be connected to the first part, wherein the first part comprises a first connection structure and the second part comprises a second connection structure, and wherein the first connection structure comprises a first outer surface and the second connection structure comprises a second outer surface which first and second outer surface are configured to, in a mounted condition, be in mutual contact with one another for transferring heat from the first part to the second part, wherein the first part and the second part are mutually connected and fastened through a spring screw mechanism having a spring screw extending in a fixed orientation parallel to the first and second outer surface.

By mean of such a light emitting device, and particularly by providing that the first part comprises a first connection structure and the second part comprises a second connection structure, and wherein the first connection structure and the second connection structure are configured to, in a mounted condition, be in mutual contact with one another for transferring heat from the first part to the second part, the heat dissipation surface area is increased considerably and the heat transfer of the light emitting device is thus improved. Hence, as explained above, feature of "the second part (configured to) being connected to the first part" is attained by the first part and the second part being (brought) in mutual contact by the first connection structure and the second connection structure. Said contact may be directly or via a heat conducting element, for example a thermal paste or graphite.

In accordance with an embodiment of the light emitting device, the first connection structure of the first part of the heat sink element comprises a first outer surface and at least one of a first protruding element and a first recessed element, and the second connection structure of the second part of the heat sink element comprises a second outer surface and at least one of a second protruding element and a second recessed element, and one or both of the first protruding element and the second recessed element, and the second protruding element and the first recessed element, are configured for mutual engagement such that in an engaged condition the first outer surface and second outer surface are abutting each other. A cross sectional view, transverse to the axis A through the first and second outer surface in the engaged condition shows an alternating or interdigitated configuration of the first and the second protruding elements. The contact between the first part and the second part established in this way improves the heat transfer from the hottest part of the light emitting device to the coldest part of the light emitting device considerably in a particularly efficient way. The heat transfer efficiency increases as the contact area increase and therefore increases also when the dimension and/or the number of the protruding and recessed elements, and thus the contact area between these elements, increases.

In accordance with an embodiment of the light emitting device, the first part comprises a first external surface adapted for connection to the housing adjacent to the light source and a first outer surface of the first connection structure extends perpendicular to the first external surface, and the second part comprises a second external surface adapted for connection to the connection surface and a second outer surface of the second connection structure extends perpendicular to the second external surface. Having such perpendicular surfaces will increase the surface area and therefore the heat transfer efficiency. Additionally, it will make the construction of the heat sink simple and the heat sink easy to assemble. Moreover, having the first external surface being adapted for connection to the light source from one side, and the second external surface being adapted for connection to the connection surface and consequently adapted for connection to the casing, improves the heat transfer from the light source to the casing and therefore increases the area for heat dissipation and the efficiency of heat transfer.

As said, the light emitting device according to the invention, the first part and the second part are mutually connected and fastened through a spring screw mechanism. Preferably said spring screw mechanism has only one axially arranged spring screw, which preferably is centrically arranged on an axis A with respect to the heat sink elements, such as concentric with concentric, cylindrically shaped recessed and protruding elements. Said axis A extends parallel to the first and second outer surface, and optionally perpendicular to the first and second external surface. The spring screw (or bolt) rests with its head on one of the first part and second part and extends with its shank and threaded portion through said part into the other part, which other part functions as a nut. The spring screw mechanism facilitates the mounting of the light emitting device, and additionally provides an easy, reliable and stable way to tune the mutual connection between the first part and the second part and thus to adjust the geometry of the heat sink element. In accordance with an embodiment of the light emitting device at least one of the first part and the second part comprises an air venting hole. This solution maximizes the contact area between the first part and the second part, and therefore the heat transmission efficiency, and allows the escape of air trapped between the first part and the second part. This solution has the advantage that it enables the first part and second part to shift mutually freely in a translational direction parallel to the first and second outer surface while still maintaining a reliable and safe connection and fastening between the first and second part. Said mutually freely shift could, for example, be the result of a difference in thermal expansion of, or a deliberate change in distance between, the housing and the casing of the light emitting device. Furthermore, said translational shift is possible while still a good mutual contact is maintained between the contact areas, i.e. between the first and second outer surface of the first and second part. Hence, this solution has the further advantage that it can be used for a wide variety of shapes of heat sinks, for example, in that it is also suitable for heat sink elements comprising concentric, cylindrically shaped recessed and protruding elements, such as cylinders with a round or square-shaped cross-sectional shape.

In accordance with an embodiment of the light emitting device, the first part and the second part comprise, in a mounted configuration, a cavity for hosting a spring element, and the light emitting device comprises a spring element arranged in the cavity for hosting a spring element. This solution allows at the same time a robust and stable heat sink element and an adaptive heat sink element solution where small tolerances and variations in geometry, i.e. materials expansions due to temperatures change, vibrations, impact, mounting condition, can be easily accommodated.

In accordance with an embodiment of the light emitting device, at least one of a thermal paste, a graphite powder, a graphite pasta, a thermal grease and a silicone oil covers fully or partially the first part and the second part when mutually in contact for heat transferring. This solution ensures that all the area between the first part and the second part is in contact through a heat conducting element and therefore the maximum heat transfer efficiency is guaranteed and further typically provides an improved, smooth mutual sliding of the first connection structure and the second connection structure.

In accordance with an embodiment of the light emitting device the heat sink element is made by cold forging. This solution ensures a simple production process and a particularly robust heat sink element. Furthermore, cold forging allows for creating straight walls of the connection structures which allows for easy movement of the heat sink parts with respect to each other in a direction parallel with the straight walls, for instance when adjusting their mutual position. Also, cold forging allows for using highly thermally conductive materials with a conductivity of around 220 W/mK. Alternatively, the light emitting device the heat sink element is made by 3D printing. This solution also ensures a simple production process and a particularly robust heat sink element.

In accordance with an embodiment of the light emitting device the heat sink element comprises fins. Fins advantageously further improves the heat transfer efficiency.

In accordance with an embodiment of the light emitting device at least one of the first part and the second part comprises one or more of: one or more vapor chambers, and one or more heat pipes. Vapor chambers and heat pipes are a great solution for improving heat transfer efficiency. Particularly, vapor chambers and heat pipes each actively and efficiently transfer heat from the hottest point or area of the light emitting device to the least hot point or area.

In accordance with an embodiment of the light emitting device, the first part and the second part comprise an interface, and the interface is partially or fully textured. This solution ensures an even larger contact area and therefore improves the heat transfer efficiency further.

In accordance with an embodiment of the light emitting device, the first protruding element, the first recessed element, the second protruding element and the second recessed element comprise a surface texture which is sine wave shaped or comprises grooves. This solution ensures a particularly large contact area and a high number of contact points and therefore improves the heat transfer efficiency.

The invention further relates to a luminaire comprising a light emitting device according to the invention.

It is noted that the invention relates to all possible combinations of features recited in the claims.

Considering the above, the present invention provides a highly adaptable disinfecting light emitting device for operating such a lighting device. The disinfecting light emitting device provides high safety level, allowing ongoing disinfection even when humans and/or animals are present in the area that is being disinfected.

BRIEF DESCRIPTION OF THE DRAWINGS

Embodiments of the invention will now be described by way of example with reference to the accompanying drawings, of which.

Figure 1:
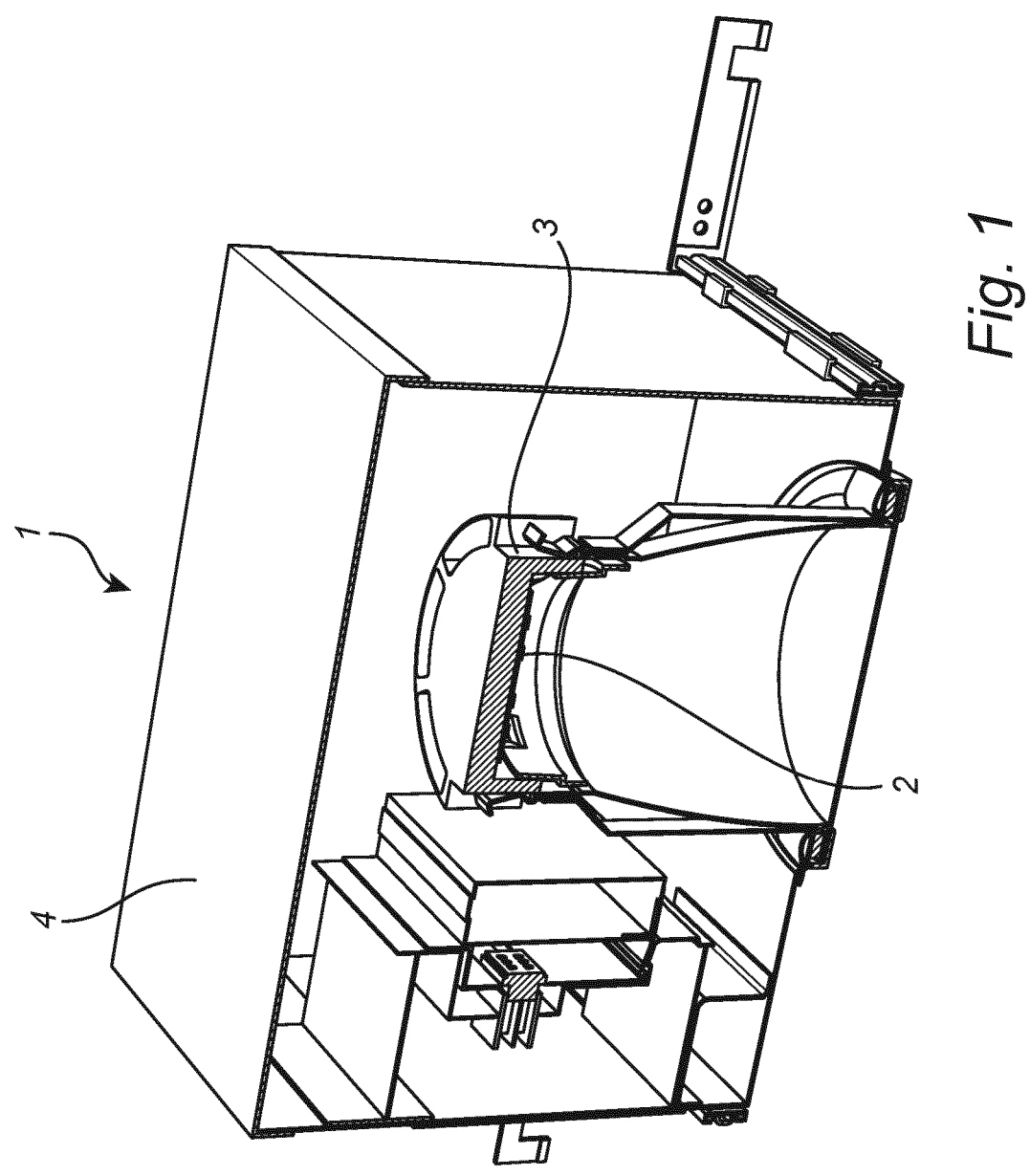
FIG. 1 shows a cross-sectional view and a perspective view of a Prior Art example.

All the figures are schematic, not necessarily to scale, and generally only show parts which are necessary in order to elucidate embodiments of the present invention, wherein other parts may be omitted or merely suggested.

DETAILED DESCRIPTION

The present invention will now be described hereinafter with reference to the accompanying drawings, in which exemplifying embodiments of the present invention are shown. The present invention may, however, be embodied in many different forms and should not be construed as limited to the embodiments of the present invention set forth herein; rather, these embodiments of the present invention are provided by way of example so that this disclosure will convey the scope of the invention to those skilled in the art. In the drawings, identical or similar reference numerals denote the same or similar components having a same or similar function, unless specifically stated otherwise.

FIG. 1 shows a cross-sectional view and a perspective view of a Prior Art example. A light emitting device 1 according to the prior art comprises a light source 2, a housing 3 and a casing 4.

Figure 2:
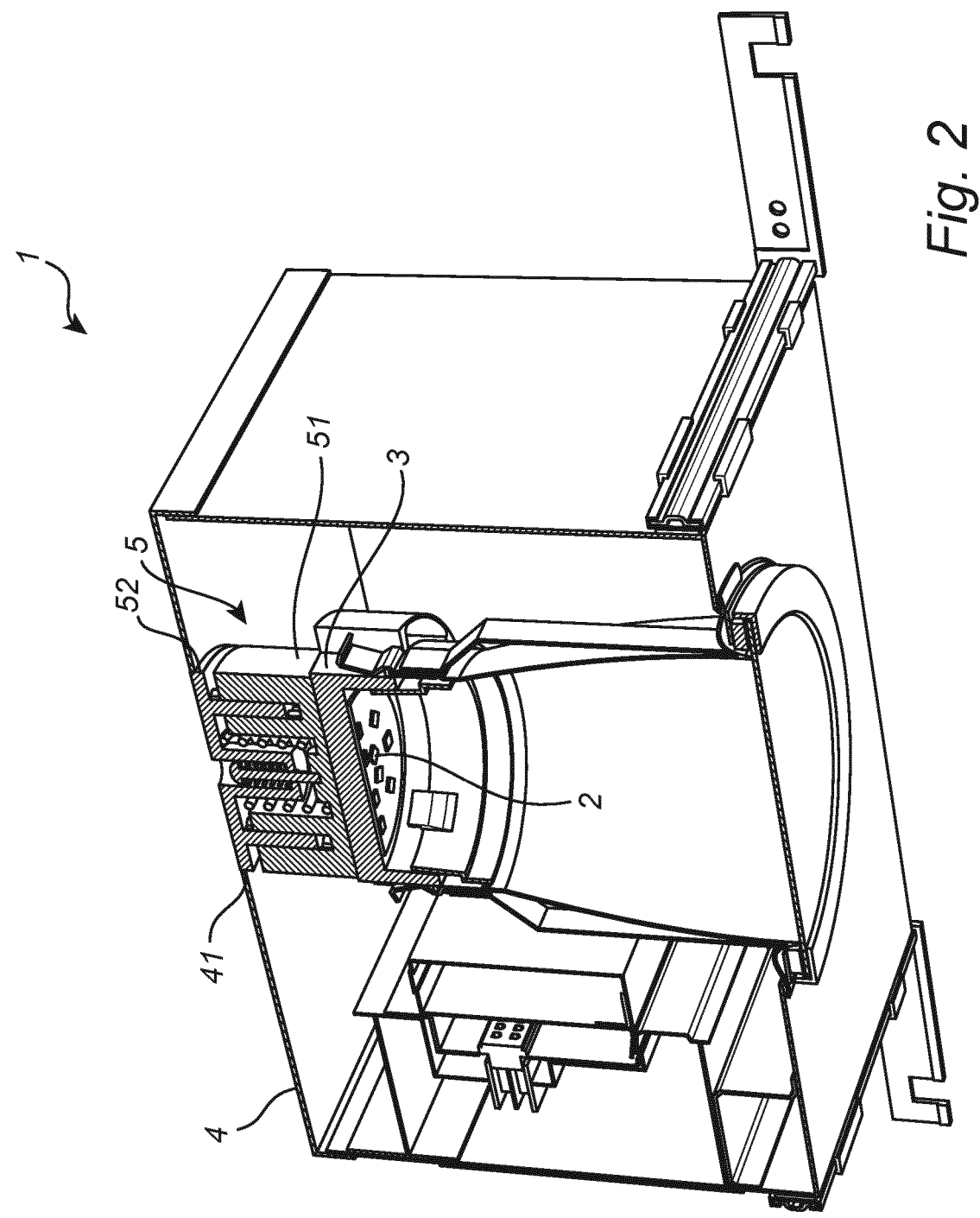
FIG. 2 shows a cross-sectional, perspective view of a light emitting device according to the invention and comprising a heat sink element.

FIG. 2 shows a cross-sectional perspective view of a light emitting device 1 according to the invention. The light emitting device 1 according to the invention generally and irrespective of the embodiment comprises a light source 2, a housing 3, a casing 4 and a heat sink element 5. The casing 4 comprises a connection surface 41. The heat sink element 5 comprises a first part 51 configured to be connected to the light source 2, and a second part 52 configured to be connected to the first part 51. The second part 52 is further configured to be connected to the connection surface 41 of the casing 4.

Generally, and irrespective of the embodiment, the casing 4 may be any type of casing including a simple casing and a junction box. The light emitting device 1 may be directly connected to a heat removal surface, which may or may not form a part of the casing 4.

The light source 2 is a solid-state light source such as an LED or a laser. The light source 2 may be arranged on a substrate, such as a PCB, suitable for accommodating electrical circuitry for connecting the light source 2 to a power source and to circuitry, such as a controller, provided in the casing 4.

Generally, the heat sink element according to the embodiments shown on the drawing is cylindrical with a round cross-sectional shape. However, other cross-sectional shapes, such as but not limited to square and rectangular in cross-sectional shape, are also possible. For instance, a heat sink element with a rectangular shape may be applied in an extruded (tube) luminaire.

Figure 3:
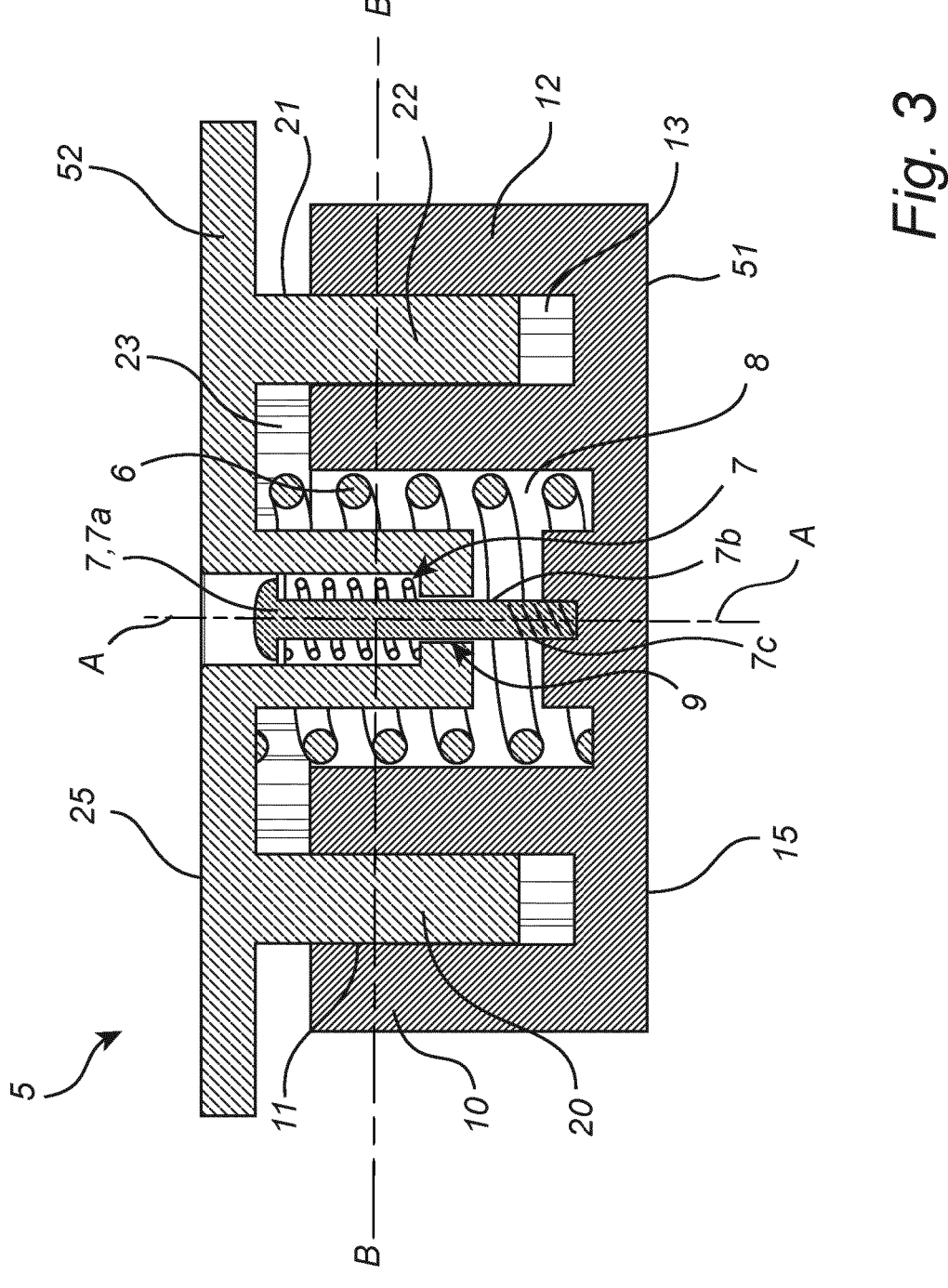
FIG. 3 shows a cross-sectional view of the heat sink element according to an embodiment of the invention.

FIG. 3 shows a cross-sectional view of the heat sink element 5 according to one embodiment of the invention. The heat sink element 5 comprises a first part 51 and a second part 52 configured to be connected to the first part 51. The first part 51 comprises a first connection structure 10 and the second part 52 comprises a second connection structure 20. The first connection structure comprises a first outer surface 11 and at least one of a first protruding element 12 and a first recessed element 13. The second connection structure 20 comprises a second outer surface 21 and at least one of a second protruding element 22 and a second recessed element 23. The first part 51 comprises a first external surface 15. The first connection structure 10 comprises a first outer surface 11. The first outer surface 11 of the first connection structure 10 extends perpendicular to first external surface 15. The second part 52 comprises a second external surface 25. The second connection structure 20 comprises a second outer surface 21. The second outer surface 21 of the second connection structure 20 extends perpendicular to the second external surface 25. A spring screw mechanism 7 with only a single spring screw connects and mutually fastens the first part 51 and the second part 52 and is centrically arranged on an axis A with respect to the concentric, cylindrically shaped recessed 23 and protruding elements 22 and extends in a fixed orientation parallel to the first 11 and second outer surface 21. The spring screw 7 (or bolt) rests with its head 7a on the second part 52 and extends with its shank 7b and threaded portion 7c through the second part 52 into the first part 51, which first part 51 functions as a nut. This solution enables the first part 51 and second part 52 to mutually shift in a translational direction, i.e. a translational shift along axis A perpendicular to the first 15 and second external surface 25, while still maintaining good mutual contact between the contact areas, i.e. the first 11 and second outer surface 21. In the figure the heat sink element 5 comprises cylindrically shaped recessed 23 and protruding elements 22, which are concentric around axis A. In particular this solution has the advantage that it can be used for a wide variety of shapes of heat sinks, for example, in that it is also suitable for concentric, cylindrically shaped heat sinks, such as cylinders with a round cross-sectional shape. An air venting hole 9 is shown in the center part of the heat sink element 5. The first part 51 and the second part 52 in a mounted configuration comprise a cavity 8 for hosting a spring element 6.

The first connection structure 10 and the second connection structure 20 are adapted for mutual engagement such that the first protruding element 12 engage in the second recessed element 23 and such that the second protruding element 22 engage in the first recessed element 13. Thereby, the first outer surface 11 of the first connection structure 10 and the second outer surface 21 of the second connection structure 20 are brought into abutment with one another, thus forming a large heat transferring transition between the first part 51 and the second part 52 of the heat sink element. The cross sectional view (along line B-B transverse to the axis A) through the first 11 and second outer surface 21 in the engaged condition shows an alternating or interdigitated configuration of the first 12 and the second protruding elements 22.

Figure 4A:
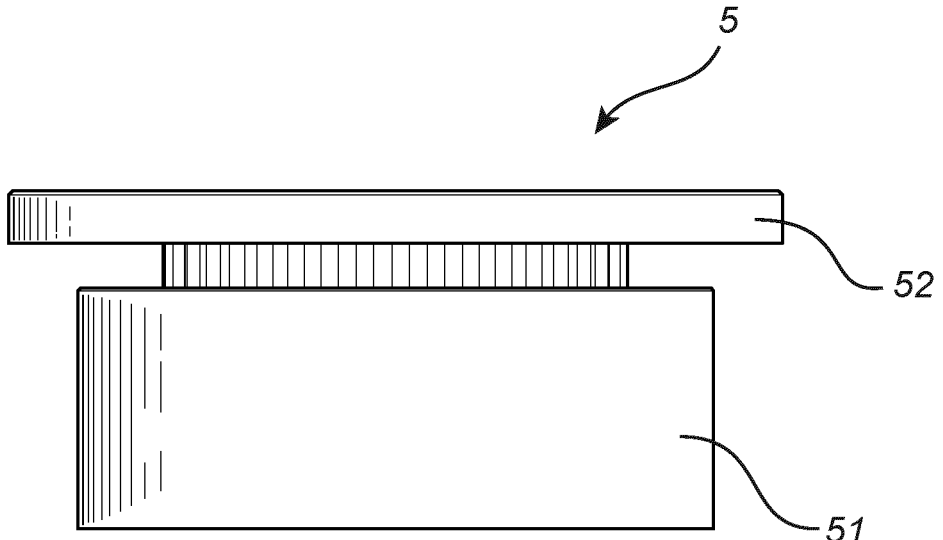
FIG. 4A and FIG. 4B show a side view and cross-sectional view, respectively, of the heat sink element according to another embodiment of the invention.
Figure 4B:
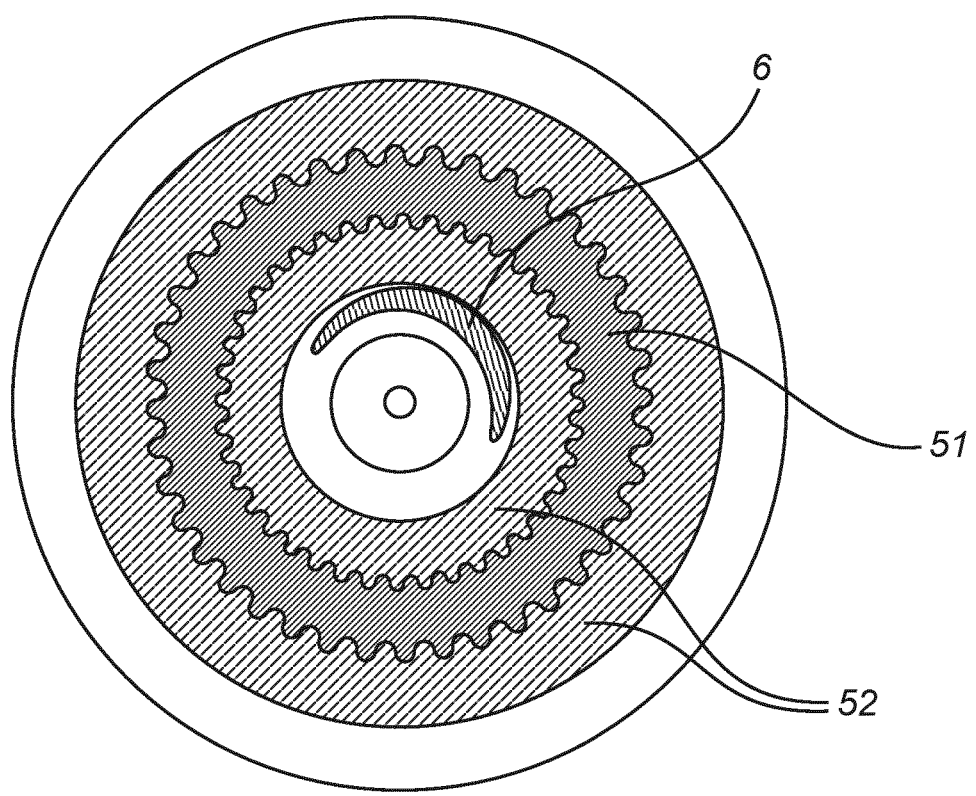
Figure 5:
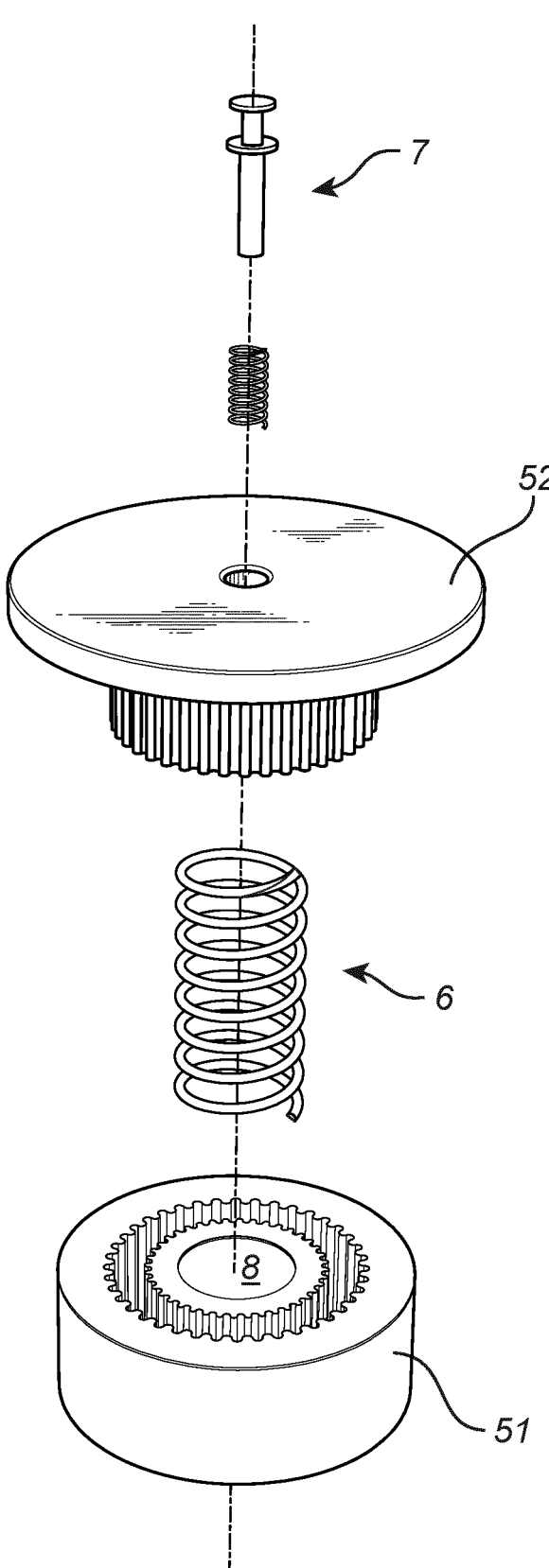
FIG. 5 shows an exploded view of the heat sink element according to FIG. 4.

FIG. 4A and FIG. 4B show a side view and cross-sectional view, respectively, while FIG. 5 shows an exploded view, of the heat sink element 5 according to another embodiment of the invention. In this embodiment the heat sink element differs from that shown in FIG. 3 in that the first part 51 and the second part 52, and more particularly the recessed and protruding elements 12, 13, 22, 23, are provided with a sine wave shaped surface structure. Put in other words, at least a part of the first outer surface 11 of the first connection structure 10 and the second outer surface 21 of the second connection structure 20 are provided with a sine wave shaped surface structure. As a reference the top view of the spring element 6 is shown. FIG. 5 further shows the spring element 6 and spring screw mechanism 7.

Figure 6:
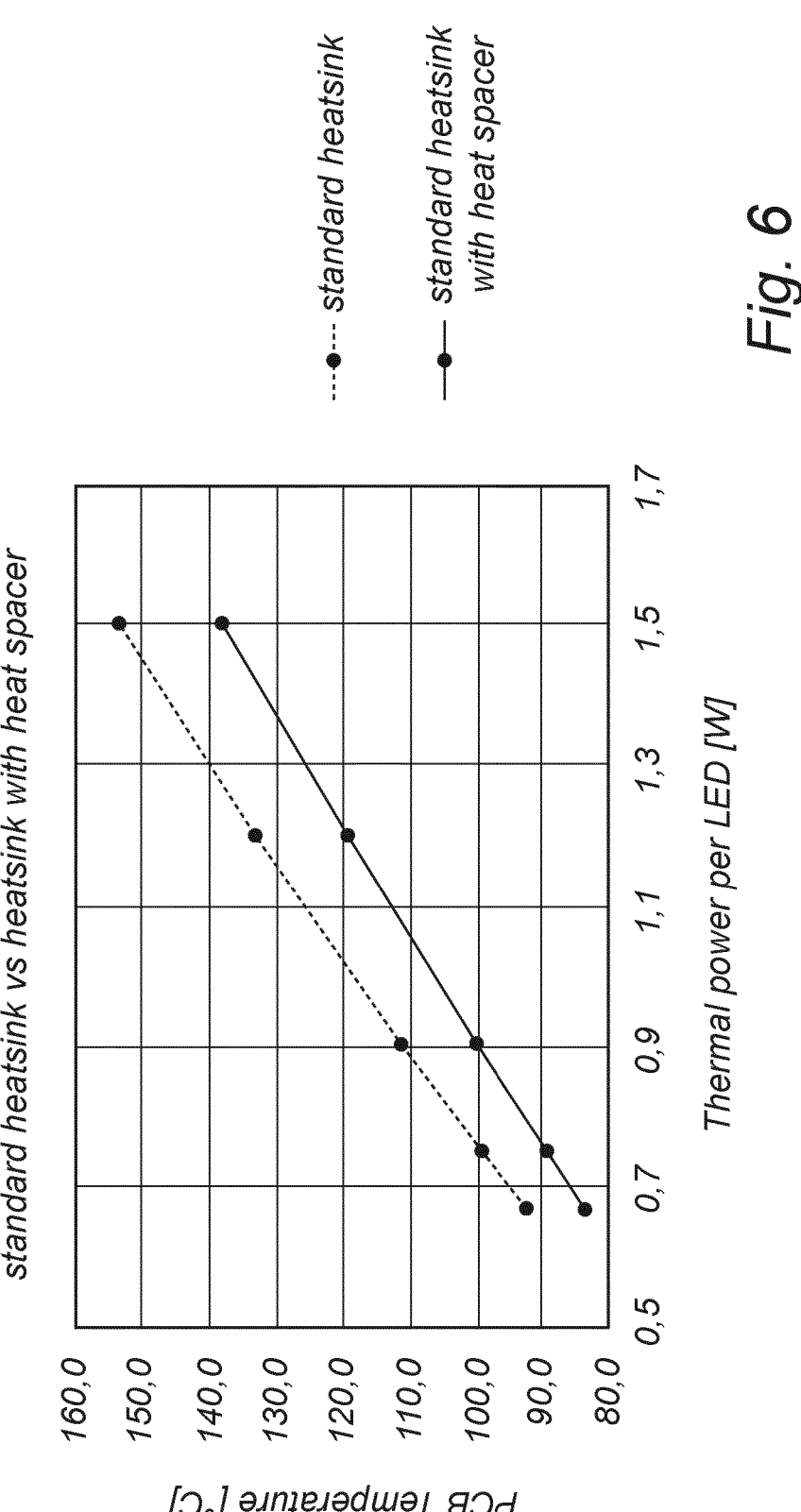
FIG. 6 shows a graph of the temperature measured at a PCB of a light emitting device as a function of the thermal power per LED and illustrating the performance of a heat sink according to one embodiment of the invention and according to the prior art, respectively.

FIG. 6 shows a graph of the temperature measured at a PCB of a light emitting device as a function of the thermal power per LED and illustrating the performance of a heat sink according to one embodiment of the invention and according to the prior art, respectively. The uppermost line shows the heat transfer performance of the prior art heatsink solution, while the lowermost line shows the heat transfer performance of one of the embodiments of the invention.

Figure 7A:
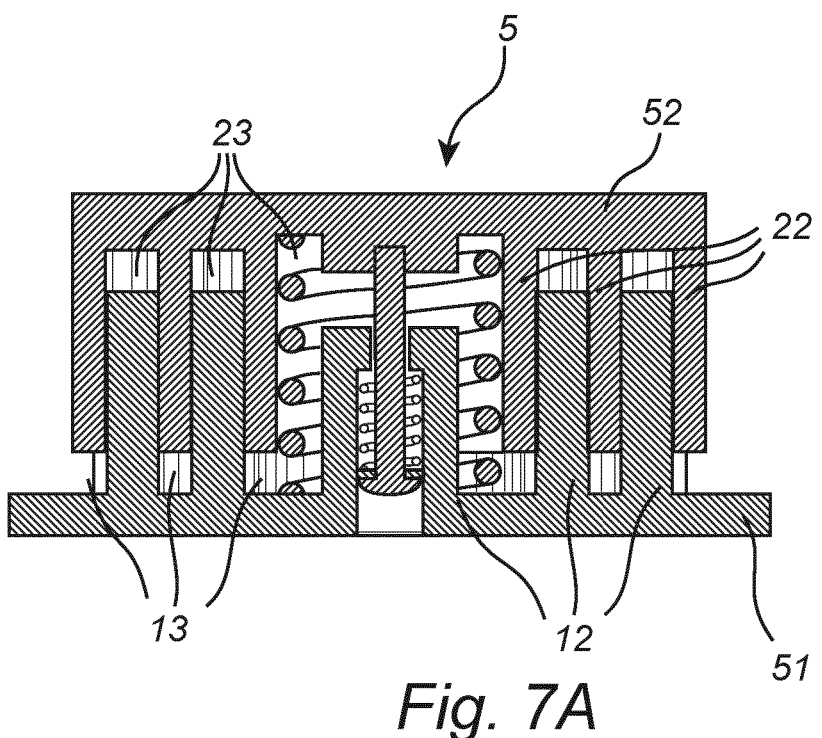
FIG. 7A and FIG. 7B show a cross-sectional side view and top view, respectively, of the heat sink element according to another embodiment of the invention.
Figure 7B:
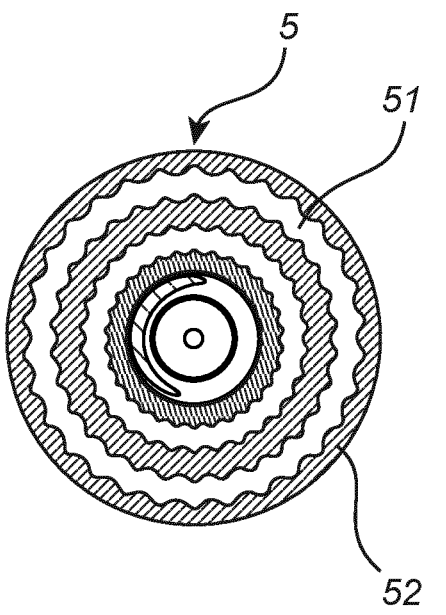

FIG. 7A and FIG. 7B show a cross-sectional view and an exploded view, respectively, of the heat sink element 5 according to another embodiment of the invention. In this embodiment the heat sink element differs from that shown in FIG. 3 in that the first element 51 and the second element 52 are provided with a sine wave shaped surface structure. The first part 51 further comprises three first protruding elements 12 and three first recessed elements 13, and the second part 52 further comprises three second protruding elements 22 and three second recessed elements 23. In this way, and as may be seen on FIG. 7B, the surface area forming the first outer surface 11 of the first connection structure 10 and the second outer surface 21 of the second connection structure 20 is increased considerably, particularly doubled as compared to the embodiment shown in FIG. 3.

Figure 8A:
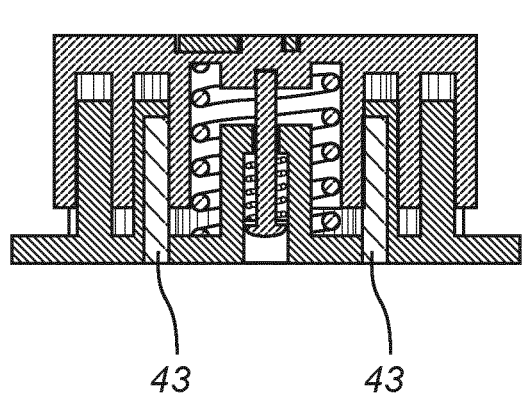
FIG. 8A and FIG. 8B show a cross-sectional view and an exploded view, respectively, of the heat sink element according to another embodiment of the invention.
Figure 8B:
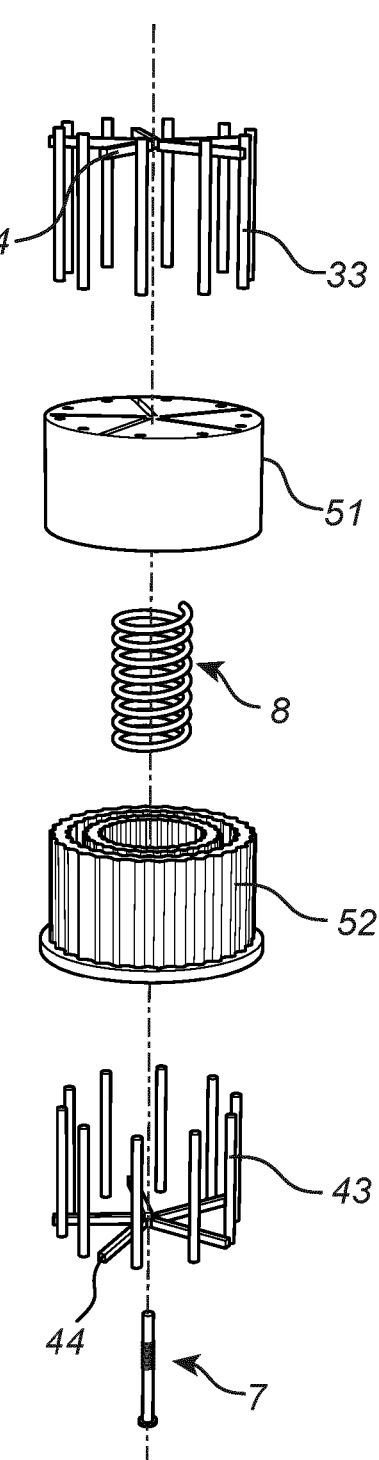

FIG. 8A and FIG. 8B show a cross-sectional view and an exploded view, respectively, of a heat sink element 5 according to another embodiment of the invention. In this embodiment the heat sink element 5 differs from that shown in FIGS. 4A, 4B and 5 in that the first part 51 and the second part 52 are respectively adapted for hosting a heat pipes 33 and 43 and vapor chambers 34 and 44. As a reference the spring element 6 and spring screw mechanism 7 are shown.

Figures 9A, 9B:
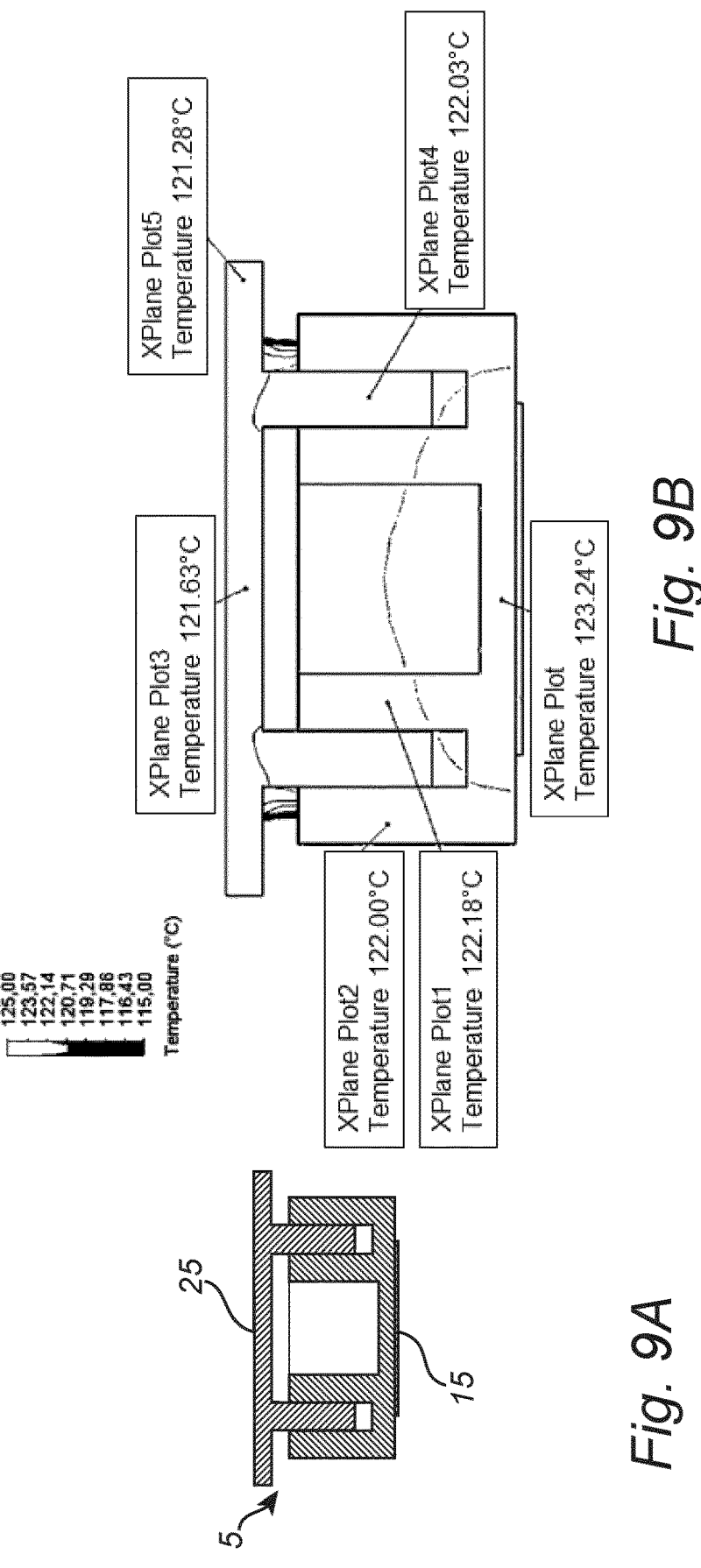
FIG. 9A and FIG. 9B show a cross-sectional view and a temperature simulation plot, respectively, of the heat sink element according to FIG. 3.

FIG. 9A and FIG. 9B show a cross-sectional view and simulation plot, respectively, of the heat sink element 5 according to one embodiment of the invention. FIG. 9A shows a cross-sectional view of a specific heat sink element 5 which is similar to the heat sink element 5 shown in FIG. 3 and described above. FIG. 9B shows the heat transfer performance of the heat sink element 5 shown in FIG. 9A by simulation of the surface temperature of the heat sink element. As may be seen, the temperature difference between the first external surface 15 and the second external surface 25 of the heat sink is kept low demonstrating a good heat transfer performance. The simulation is run with a 25 W thermal power source resulting in an average heat sink temperature of about 122° C.

Figures 10A, 10B:
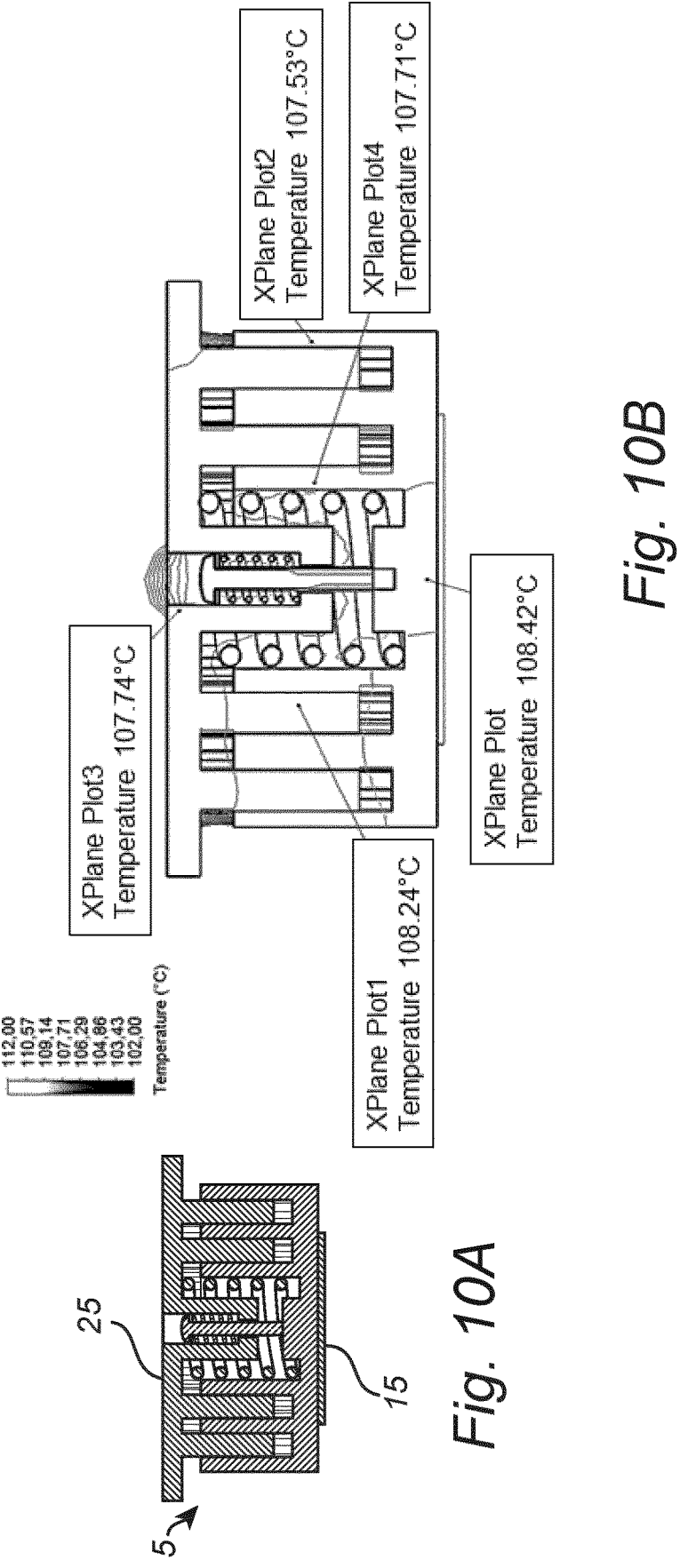
FIG. 10A and FIG. 10B show a cross-sectional view and a temperature simulation plot, respectively, of the heat sink element according to FIG. 7.

FIG. 10A and FIG. 10B show a cross-sectional view and simulation plot, respectively, of the heat sink element 5 according to one embodiment of the invention. FIG. 10A shows a cross-sectional view of a specific heat sink element 5 which is similar to the heat sink element 5 shown in FIGS. 7A and 7B and described above. FIG. 10B shows the heat transfer performance of the heat sink element 5 shown in FIG. 10A by simulation of the surface temperature of the heat sink element. As may be seen, the temperature difference between the first external surface 15 and the second external surface 25 of the heat sink is kept low demonstrating a good heat transfer performance. The simulation is run with a 25 W thermal power source resulting in an average heat sink temperature of about 108° C.

Figures 11A, 11B:
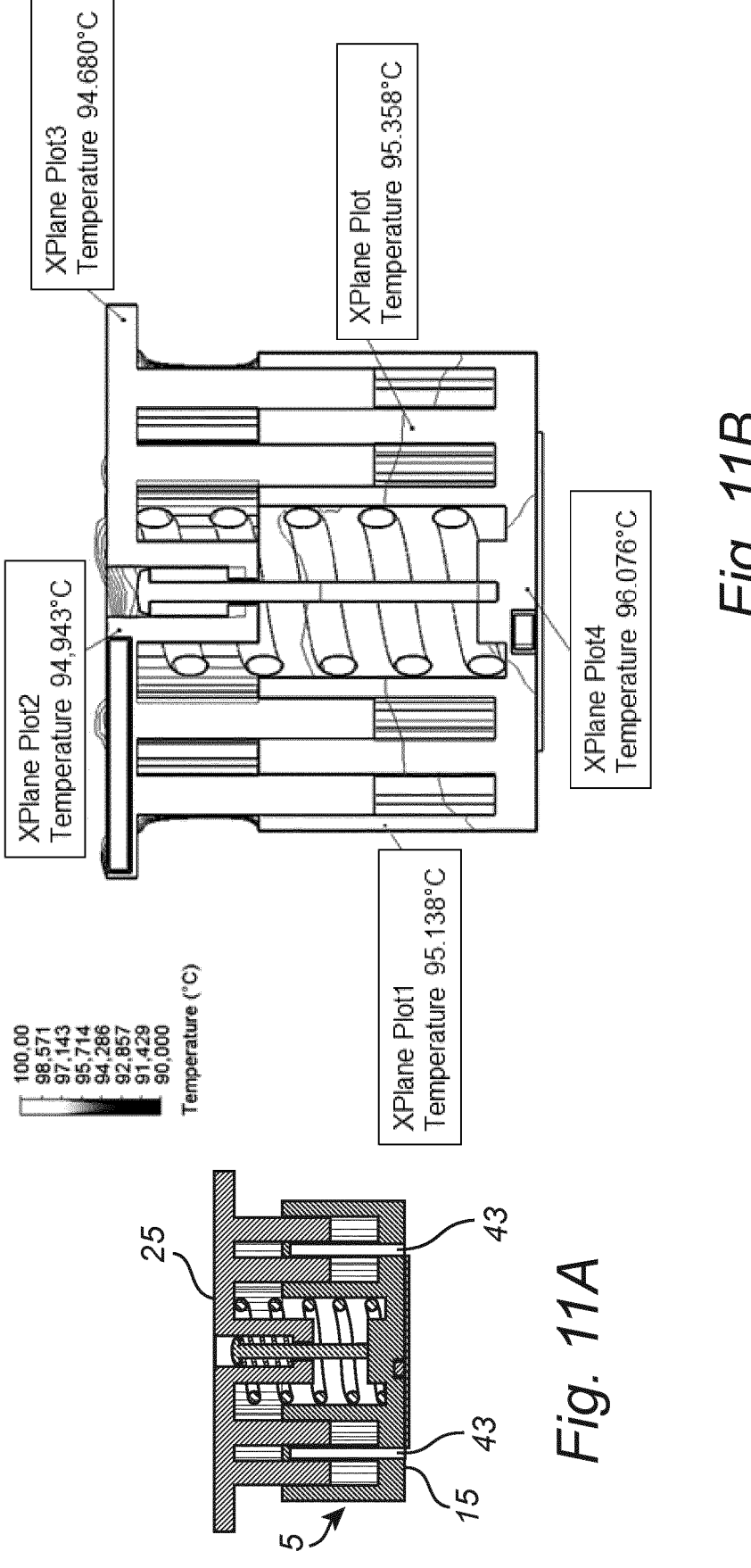
FIG. 11A and FIG. 11B show a cross-sectional view and simulation plot, respectively, of the heat sink element according to FIG. 8 and comprising heat pipes.

FIG. 11A and FIG. 11B show a cross-sectional view and simulation plot, respectively, of the heat sink element 5 according to one embodiment of the invention. FIG. 11A shows a cross-sectional view of a specific heat sink element 5 which is similar to the heat sink element 5 shown in FIGS. 8A and 8B and described above albeit comprising heat pipes only. FIG. 11B shows the heat transfer performance of the heat sink element 5 shown in FIG. 11A by simulation of the surface temperature of the heat sink element. As may be seen, the temperature difference between the first external surface 15 and the second external surface 25 of the heat sink is kept low demonstrating a good heat transfer performance. The simulation is run with a 25 W thermal power source resulting in an average heat sink temperature of about 95° C.

Figures 12A, 12B:
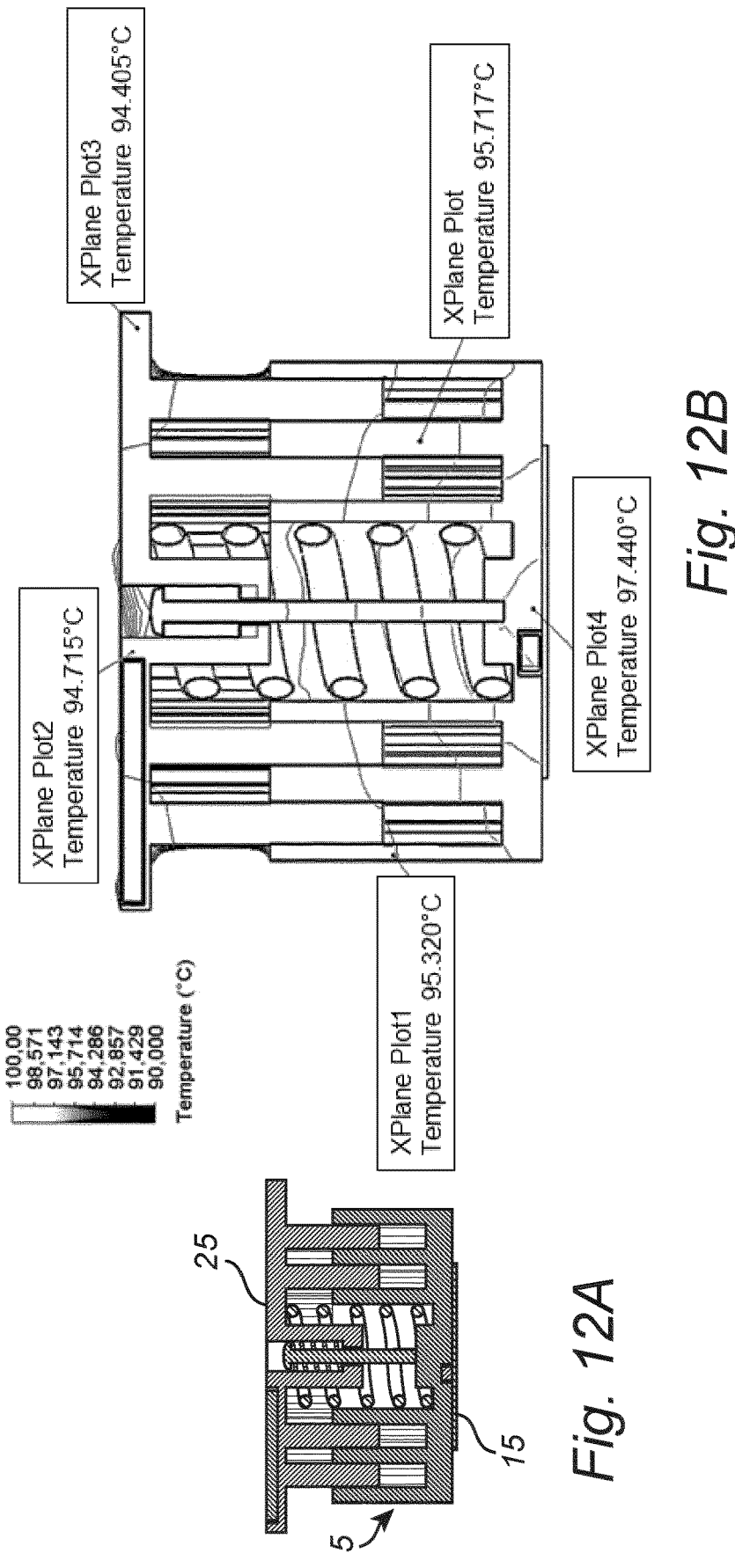
FIG. 12A and FIG. 12B show a cross-sectional view and a temperature simulation plot, respectively, of the heat sink element according to FIG. 8 but without heat pipes.

FIG. 12A and FIG. 12B show a cross-sectional view and simulation plot, respectively, of the heat sink element 5 according to one embodiment of the invention. FIG. 12A shows a cross-sectional view of a specific heat sink element 5 which is similar to the heat sink element 5 shown in FIGS. 8A and 8B and described above albeit comprising no heat pipes. FIG. 9B shows the heat transfer performance of the heat sink element 5 shown in FIG. 12A by simulation of the surface temperature of the heat sink element. As may be seen, the temperature difference between the first external surface 15 and the second external surface 25 of the heat sink is kept low demonstrating a good heat transfer performance. The simulation is run with a 25 W thermal power source resulting in an average heat sink temperature of about 97° C.

Although the present invention has been described with reference to various embodiments, those skilled in the art will recognize that changes may be made without departing from the scope of the invention. It is intended that the detailed description be regarded as illustrative and that the appended claims including all the equivalents are intended to define the scope of the invention. While the present invention has been illustrated in the appended drawings and the foregoing description, such illustration is to be considered illustrative or exemplifying and not restrictive; the present invention is not limited to the disclosed embodiments.

Other variations to the disclosed embodiments can be understood and effected by those skilled in the art in practicing the claimed invention, from a study of the drawings, the disclosure, and the appended claims. In the appended claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light emitting device comprising a light source, a housing, a casing and a heat sink element, the casing comprising a connection surface, the heat sink element comprising a first part configured to be connected to the light source, and a second part configured to be connected to the first part, wherein the first part comprises a first connection structure and the second part comprises a second connection structure, and wherein the first connection structure comprises a first outer surface and the second connection structure comprises a second outer surface which first and second outer surface are configured to, in a mounted condition, be in mutual contact with one another for transferring heat from the first part to the second part, wherein the first part and the second part are mutually connected and fastened through a spring screw mechanism having a spring screw and extending in a fixed orientation parallel to the first and second outer surface, wherein the first part comprises a first external surface adapted for connection to the housing adjacent to the light source and the first outer surface of the first connection structure extends perpendicular to first external surface, and the second part comprises a second external surface adapted for connection to the connection surface and the second outer surface of the second connection structure extends perpendicular to the second external surface, and wherein the spring screw is configured to tune the mutual connection between the first part and the second part to increase or decrease a surface area connection of the first external surface and second external surface and thereby adjust a thermal property of the heat sink.

2. The light emitting device according to claim 1, wherein the first connection structure of the first part of the heat sink element comprises at least one of a first protruding element and a first recessed element, and the second connection structure of the second part of the heat sink element comprises at least one of a second protruding element and a second recessed element, and one or both of the first protruding element and the second recessed element, and the second protruding element and the first recessed element, are configured for mutual engagement such that in an engaged condition the first outer surface and second outer surface are abutting each other.

3. The light emitting device according to claim 1, wherein the spring screw mechanism having only one axially arranged spring screw along an axis A, said axis A and said spring screw extending parallel to the first and the second outer surface, wherein said spring crew is centrically arranged on said axis A.

4. The light emitting device according to claim 1, wherein at least one of the first part and the second part comprise an air venting hole.

5. The light emitting device according to claim 1, wherein the first part and the second part in a mounted configuration comprise a cavity for hosting a spring element.

6. The light emitting device according to claim 1, wherein at least one of a thermal paste, a graphite powder, a graphite paste, a thermal grease and a silicone oil covers fully or partially the first part and the second part when mutually in contact for heat transferring.

7. The light emitting device according to claim 1, wherein the heat sink element is made by cold forging or by 3D printing.

8. The light emitting device according to claim 1, wherein the heat sink element comprises fins.

9. The light emitting device according to claim 1, wherein at least one of the first part and the second part comprises one or more of:

one or more vapor chambers, and one or more heat pipes.

10. The light emitting device according to claim 1, wherein the first part and the second part comprise an interface, and wherein the interface is partially or fully textured.

11. The light emitting device according to claim 1, wherein the first protruding element, the first recessed element, the second protruding element and the second recessed element comprise a surface texture which is sine wave shaped or comprises grooves.

12. A luminaire comprising a light emitting device according to claim 1.

* * * * *